(12) United States Patent
Patwardhan

(10) Patent No.: US 12,144,586 B2
(45) Date of Patent: Nov. 19, 2024

(54) VARIABLE POLARIZATION AND SKIN DEPTH ANALYSIS METHODS AND APPARATUSES

(71) Applicant: Canfield Scientific, Incorporated, Parsippany, NJ (US)

(72) Inventor: Sachin V. Patwardhan, Mount Tabor, NJ (US)

(*) Notice: Subject to any disclaimer, the term of this patent is extended or adjusted under 35 U.S.C. 154(b) by 2 days.

(21) Appl. No.: 17/010,615

(22) Filed: Sep. 2, 2020

(65) Prior Publication Data

US 2021/0059533 A1    Mar. 4, 2021

Related U.S. Application Data

(60) Provisional application No. 62/894,939, filed on Sep. 2, 2019.

(51) Int. Cl.
*G06T 7/55* (2017.01)
*A61B 5/00* (2006.01)
(Continued)

(52) U.S. Cl.
CPC .......... *A61B 5/0082* (2013.01); *A61B 5/0077* (2013.01); *A61B 5/441* (2013.01);
(Continued)

(58) Field of Classification Search
CPC .................. H04N 5/2354; G06T 15/08; G06T 2207/30088; G06T 2210/41; G06T 7/0012;
(Continued)

(56) References Cited

U.S. PATENT DOCUMENTS

| 8,058,608 B1* | 11/2011 | Deason ................. B23K 31/12 |
| | | 359/251 |
| 10,078,254 B2* | 9/2018 | Higashitsutsumi .. A61B 5/0022 |

(Continued)

FOREIGN PATENT DOCUMENTS

| JP | 10333057 A1 | 12/1998 |
| JP | 2015-188579 A1 | 11/2015 |

OTHER PUBLICATIONS

PCT/US2020/049059, International Search Report and Written Opinion of the International Searching Authority, Nov. 20, 2020.

*Primary Examiner* — Jessica M Prince

(57) ABSTRACT

Methods and apparatuses are disclosed for capturing and analyzing images of tissue, such as human skin, using variable polarization. Exemplary devices are described having a detection polarizer via which an area of tissue is imaged and one or more light sources whose emitted light is polarized with one or more source polarizers. In a first such device, one or more of the detection polarizer and a source polarizer is rotatable so as to allow the angle between their polarizations to be varied. An area of tissue can be imaged as the angle is varied. Another device has multiple fixed source polarizers of different polarization orientations, each source polarizer polarizing the light emitted by a corresponding group of light sources which can be selectively activated, thereby enabling the device to illuminate an area of tissue with polarized light of different orientations relative to the orientation of the detection polarizer. Images of an area of tissue captured with different polarizations provide information from different depths, allowing visualization of superficial as well as subsurface features.

9 Claims, 10 Drawing Sheets

(51) Int. Cl.
 *G02B 27/28* (2006.01)
 *G06T 7/00* (2017.01)
 *G06T 15/08* (2011.01)
 *H04N 23/74* (2023.01)

(52) U.S. Cl.
 CPC .......... *G02B 27/281* (2013.01); *G06T 7/0012* (2013.01); *G06T 7/55* (2017.01); *G06T 15/08* (2013.01); *H04N 23/74* (2023.01); *A61B 2562/0242* (2013.01); *G06T 2207/30088* (2013.01); *G06T 2210/41* (2013.01)

(58) Field of Classification Search
 CPC . G06T 7/55; G02B 27/281; A61B 2562/0242; A61B 5/0077; A61B 5/0082; A61B 5/441

See application file for complete search history.

(56) References Cited

U.S. PATENT DOCUMENTS

| | | |
|---|---|---|
| 2004/0174525 A1* | 9/2004 | Mullani ............... A61B 5/0059 356/369 |
| 2004/0201846 A1 | 10/2004 | Mullani |
| 2014/0243685 A1* | 8/2014 | Patwardhan ............ A61B 5/44 600/476 |
| 2015/0374277 A1* | 12/2015 | Patwardhan ........... A61B 5/445 600/476 |
| 2016/0105659 A1* | 4/2016 | Hayashi ............ A61B 1/00193 348/47 |
| 2017/0052430 A1 | 2/2017 | Higashitsutsumi et al. |
| 2018/0289293 A1* | 10/2018 | Basiri ................ A61B 5/14552 |
| 2018/0368692 A1* | 12/2018 | Hong ................... A61B 5/0077 |
| 2019/0266399 A1* | 8/2019 | Kanamori ........... G06V 40/197 |
| 2019/0343450 A1* | 11/2019 | Park ..................... A61B 5/0059 |
| 2020/0117882 A1* | 4/2020 | Kozicki ............... G06V 10/147 |
| 2020/0154988 A1* | 5/2020 | Fukazawa ............. A61B 1/063 |
| 2021/0150744 A1* | 5/2021 | Sambongi ............... G06T 7/593 |
| 2021/0271061 A1* | 9/2021 | Fukazawa ............. A61B 1/045 |

* cited by examiner

VARIABLE POLARIZATION AND SKIN DEPTH ANALYSIS METHODS AND APPARATUSES

RELATED APPLICATIONS

This application claims priority from U.S. Provisional Patent Application No. 62/894,939, filed Sep. 2, 2019, which is incorporated herein by reference in its entirety.

FIELD OF THE APPLICATION

The present disclosure pertains to the capture and analysis of images of skin using polarization imaging.

BACKGROUND INFORMATION

The use of a polarizing filter in photography for reducing glare, managing reflections, and darkening skies is known. The filter can be rotated to obtain the required balance of light in the photograph. Light reflected from a non-metallic surface becomes polarized. A polarizer rotated to pass only light polarized in the direction perpendicular to the reflected light absorbs most of the reflected light and removes glare from the image.

When light is cast onto tissue, such as human skin, part of the light is transmitted into the tissue and part of the light is reflected from its surface. If the light incident onto the tissue is polarized, such as by passing it through a polarizing filter arranged between the light source and the tissue, then the surface reflection maintains the same polarization as that of the incident light. Light that enters the tissue undergoes scattering and absorption. Each photon that enters the tissue follows a random path, and due to scattering starts losing its incident polarization. The deeper into the tissue a photon travels, the more scattering it undergoes, and the greater will be the loss of its incident polarization. Some of the photons that have entered the tissue reflect back towards the skin surface and can escape out of the skin as diffuse reflectance.

Based on the above-described phenomenon, the use of parallel- and cross-polarized imaging of tissue is a commonly known technique for selectively capturing diffuse and surface reflectance, respectively. Parallel-polarized imaging is often used in skin imaging to evaluate skin topography and skin texture features, whereas cross-polarized imaging is used to evaluate subsurface features such as the distribution and concentration of skin chromophores.

Conventional cross-polarized and parallel-polarized images, however, are two-dimensional. They are projection images of photons reflected back towards the camera from various depths but with no way of differentiating depth information.

SUMMARY OF THE DISCLOSURE

The present disclosure sets out apparatuses and methods for capturing and analyzing images of tissue, such as human skin, using variable polarization. Exemplary devices are described having a detection polarizer via which an area of tissue is imaged and one or more light sources whose emitted light is polarized with one or more source polarizers. In a first such device, one or more of the detection polarizer and a source polarizer is rotatable so as to allow the angle between orientations of their polarizations to be varied. An area of tissue can be imaged as the angle is varied. Another device has multiple fixed source polarizers of different polarization orientations, each source polarizer polarizing the light emitted by a corresponding group of light sources which can be selectively activated, thereby enabling the device to illuminate an area of tissue with polarized light of different orientations relative to the orientation of the detection polarizer. Images of an area of tissue captured with different polarizations provide information from different depths, allowing visualization of superficial as well as subsurface features.

The aforementioned and other aspects of the present disclosure are set forth in greater detail below, with reference to the drawings filed herewith.

DETAILED DESCRIPTION

Figure 1:
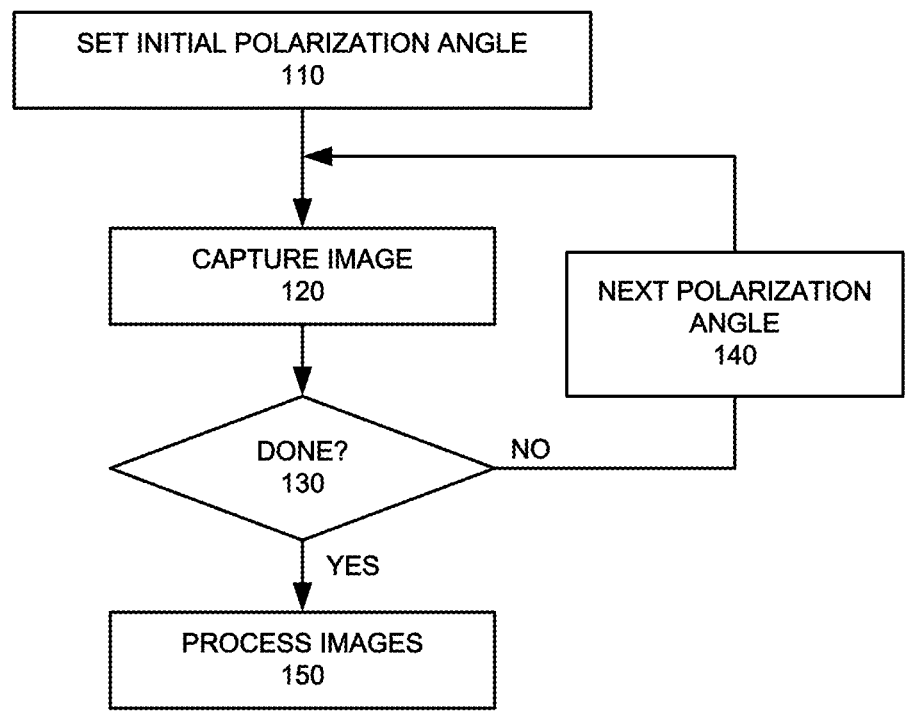
FIG. 1 is a high-level flowchart of an exemplary method in accordance with the present disclosure.

The following merely illustrates the principles of the present disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures, and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the disclosure.

In addition, it will be appreciated by those skilled in art that any flowcharts, process diagrams, and the like represent various processes which may be substantially represented in computer readable media and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flowchart elements or other elements indicating performance of process steps and/or textual description. Such modules may be executed by hardware that is expressly or implicitly shown. Additionally, although illustrated as single elements, each such block or step shown may be implemented with multiple blocks or steps, or various combinations thereof. Terms such as "software," "application," "program," "firmware," or the like, are intended to refer, without limitation, to any instruction or set of instructions, structure, or logic embodied in any suitable machine-readable medium.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture, and 3D volumetric image data may represent a stack of 2D images that represent a 3D volume of the object being imaged.

The present disclosure describes methods and apparatuses for imaging skin surface and skin subsurface features while obtaining depth information using polarization angles between 0 and 90 degrees. Unless otherwise apparent, the term "polarization angle" as used herein refers to the angle between the polarization orientation of light incident onto the skin and the orientation of polarization through which light reflected from the skin is detected. Typically, these polarizations are imparted respectively by a polarizing filter arranged between a light source and the skin, hereinafter a "source" polarizer, and another polarizing filter arranged between the skin and an image detector, hereinafter a "detection" polarizer. As such, "polarization angle" is also used herein to refer to the angle between the polarization orientations of the source and detection polarizers.

The methods and apparatuses described herein can be used to image and obtain depth information for skin surface features such as wrinkles and pores, as well as subsurface skin features such as blood vessels and chromophores.

Turning now to the drawings, FIG. 1 is a high-level flowchart of an exemplary method 100 in accordance with the present disclosure. Generally, method 100 entails capturing a series of images, each with a different polarization angle between and/or including 0 and 90 degrees. Several embodiments of apparatuses that may be used with method 100 are described further below.

In a first part 110, operation begins by setting an initial polarization angle for a source and detection polarization with which an image is to be captured. For illustrative purposes, it can be assumed that the initial polarization angle is 0, although other initial angles are possible. Part 110 includes configuring the image capture apparatus in accordance with the current polarization angle. As described further below, how this configuring is done will depend on the apparatus's implementation, such as, for example, by adjusting one or both of the orientations of the source and detection polarizers, among other possibilities.

Operation then proceeds to 120 in which an image is captured using the current polarization angle. A reflectance image of skin captures a combination of surface reflectance and diffuse reflectance. When the source and detection polarizers are parallel to each other, i.e., the polarization angle is 0 degrees, most of the captured reflectance is surface reflectance. When the source and detection polarizers are perpendicular to each other, i.e., the polarization angle is 90 degrees, most of the captured reflectance is diffuse reflectance. However, for polarization angles between 0 and 90 degrees, varying amounts of surface and diffuse reflectance are captured. As the angle between the polarizer orientations increases from 0 degrees towards 90 degrees, the surface reflectance component in the captured image will decrease and the diffuse reflectance component will increase. This will yield images having information from various depths corresponding to the average depth at which the photons have rotated by the polarization angle. With a polarization angle of about 37.5 degrees, the image obtained would look like a standard image captured with non-polarized light. With polarization angles from 0 degrees to about 52.5 degrees, the respective images will show skin textural features, moving into the depths of such features. On the other hand, if the polarization angle is changed from 90 degrees towards 0 degrees, one would see subsurface skin features, with the 90 degrees image showing the features at maximum depth and then moving towards the skin surface with decreasing polarization angle. Skin subsurface information can be captured at polarization angles between 37.5 and 90 degrees. With cross-polarization, features at depths of up to approximately 1 to 1.5 mm from the skin's surface can typically be imaged.

Figure 2:
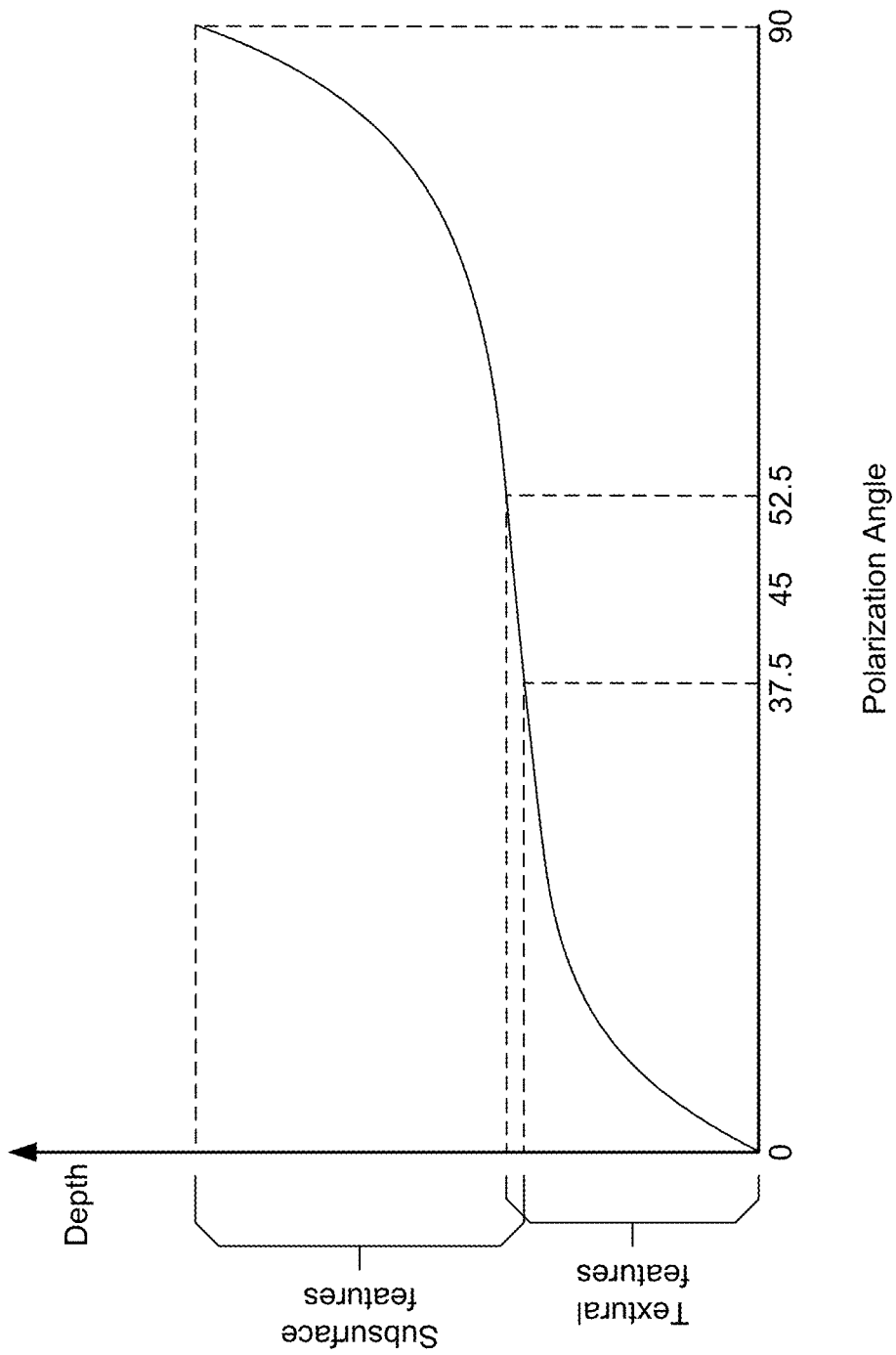
FIG. 2 is a graph showing the relationship between the polarization angle with which skin imaging is performed and the depth into the skin that is imaged thereby.

An approximation of the above-described relationship between polarization angle and depth is shown graphically in FIG. 2. The deeper into the tissue a photon travels, the more scattering it undergoes, and the greater will be the loss of its initial incident polarization. The loss of polarization of a photon is scatter-dependent, and the amount of scattering is dependent on the depth traveled by the photon. Diffuse reflectance from a particular depth, on average, would have a polarized component that has rotated by a certain amount with respect to the incident polarized source orientation. An image captured with a certain polarization angle will predominantly show features from a certain depth, which can be estimated using mathematical modeling of light-tissue interaction, such as, for example, using Monte Carlo simulations or diffusion radiative transfer models of light propagation inside tissue. An exemplary such model typically assigns certain absorption and scattering properties to various skin layers and simulates photons propagation through the layers. It bears noting, however, that different skin types (i.e., fair to dark) will exhibit different degrees of absorption, so that with higher absorption, the depths that can be imaged will be shallower. As such, while it may not be possible to assign a specific depth in absolute terms to a particular polarization angle, it is possible to reliably determine that features seen with higher polarization angles are deeper than those seen with lower polarization angles, and that features seen with lower polarization angles are shallower than those seen with higher polarization angles. In exemplary implementations, multiple skin-type-specific models can be generated, and then based on the skin type of the skin being imaged, a selected one of the models can be used to estimate feature depth from polarization angle. Using such skin-type-specific models should provide better estimates of depth than a generic model intended to cover all skin types.

Referring again to FIG. 1, once an image has been captured at 120 with a particular polarization angle, operation then proceeds to 130 in which a determination is made as to whether or not all of the images of the desired series of images have been captured; i.e., using all of the desired polarization angles. If not, operation proceeds to 140 in which the next polarization angle for the series of images is selected and the image capture apparatus configured accordingly. Operation then continues, as before, to 120 to capture the next image with the new polarization angle.

Figure 8A:
FIGS. 8A and 8B show two exemplary series of images captured at successively greater polarization angles from 0 to 90 degrees.
Figure 8A:
Figure 8A:
Figure 8A:
Figure 8A:
Figure 8A:
Figure 8A:
Figure 8A:
Figure 8A:
Figure 8B:
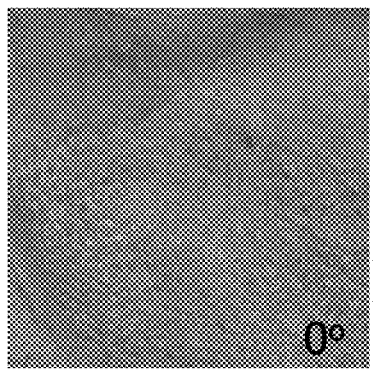
Figure 8B:
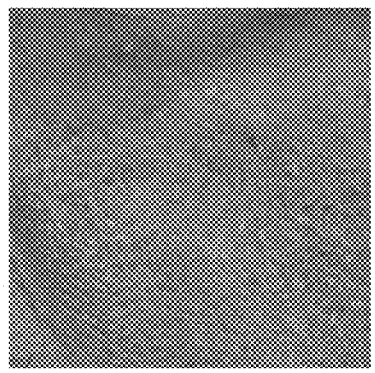
Figure 8B:
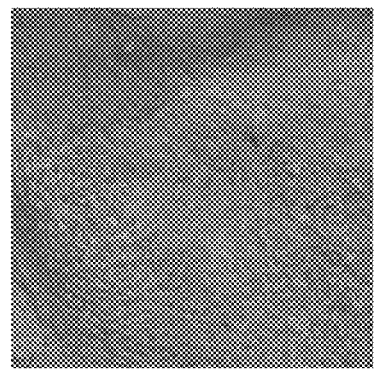
Figure 8B:
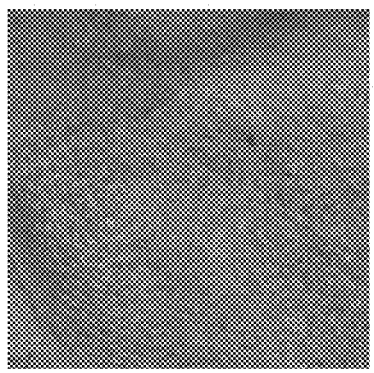
Figure 8B:
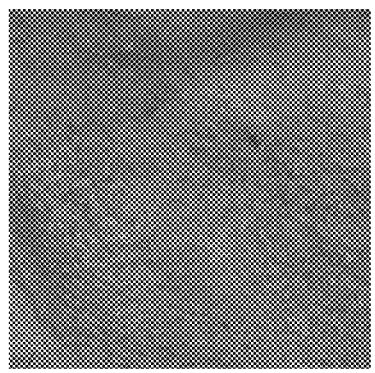
Figure 8B:
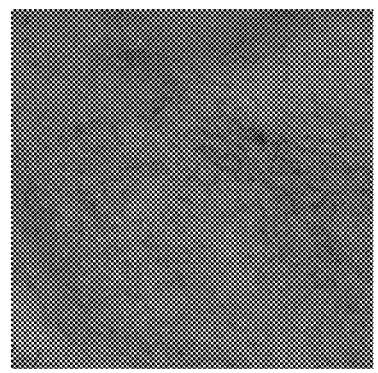
Figure 8B:
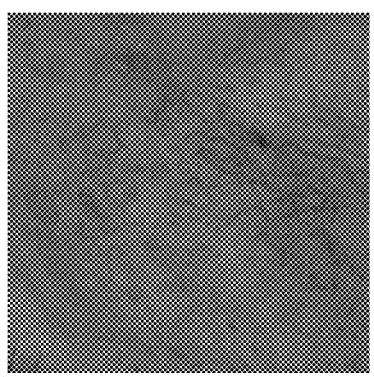
Figure 8B:
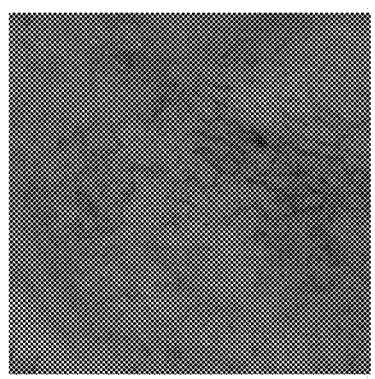
Figure 8B:
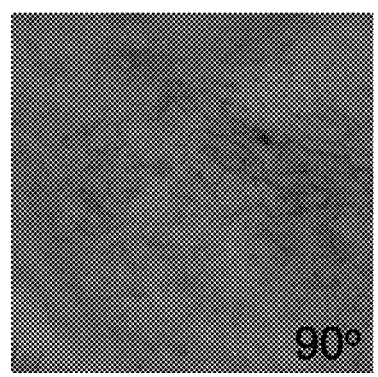

Once it is determined at 130 that all of the images of the series have been captured, operation proceeds to 150 in which the series of images are processed. FIG. 8A shows an illustrative such series of images captured at successively greater polarization angles from 0 to 90 degrees, at substantially equal increments. The series of images of FIG. 8A illustrate how superficial features, such as wrinkles, while clearly visible with smaller polarization angles, become less visible, if at all, with larger polarization angles. Another series of captured images, shown in FIG. 8B, illustrate how subsurface features, such as vascular structures, become increasingly visible at greater polarization angles.

Processing 150 may include a variety of operations, including displaying, storing and/or communicating the images as captured or processed, and/or further images, measurements, and/or metrics derived from the images.

Processing at 150 may include, for example, performing registration of the images for further processing, as described below, in which information is extracted by processing two or more images. Processing may include adjusting color and/or intensity levels of the images to ensure that they are similar in color and intensity. Additionally, with more diffuse reflectance, images will become soft and thus sharpening them may be desirable. Furthermore, for deeper imaging with larger polarization angles, it may be desirable to compensate for the loss of light at greater depths due to absorption and scattering away from the camera. Accordingly, depth-dependent sharpening and/or intensity compensation using known techniques preferably can be applied in processing 150.

Additionally, processing may include performing various operations using a combination of images to selectively enhance and detect features at specified depth(s). This may entail obtaining information from specific depths by subtracting images captured with different polarization angles.

More specifically, an image captured with parallel polarization (i.e., with polarization angle 0) shows all superficial features, such as wrinkles and pores, up to a certain depth. A further image captured with a somewhat greater polarization angle (e.g., 10 degrees) will show all but the most superficial features (e.g., all but the upper ridges of the wrinkles) shown in the parallel polarized image. Similarly, additional images captured with successively greater polarization angles, will show progressively fewer superficial features, or parts thereof. This progression is illustrated in the series of images shown in FIG. 8A. As such, if an image $I_n$ captured with a polarization angle corresponding to a depth $D_n$ is subtracted from an image $I_{n-1}$ captured with a polarization angle corresponding to a depth $D_{n-1}$, where $D_n > D_{n-1}$, the resultant image $I_{n-1} - I_n$ will isolate or emphasize those features lying at or about depth $D_{n-1}$.

Similarly, an image captured with cross polarization (i.e., with polarization angle 90) shows subsurface features up to a certain depth, including any intervening features at shallower depths. A further image captured with a somewhat smaller polarization angle (e.g., 80 degrees) will show all but the deepest features shown in the cross polarized image. Similarly, additional images captured with successively smaller polarization angles, will show progressively fewer subsurface features, or parts thereof. This progression is illustrated in the series of images shown in FIG. 8B. As such, if an image $I_n$ captured with a polarization angle corresponding to a depth $D_n$ is subtracted from an image $I_{n-1}$ captured with a polarization angle corresponding to a depth $D_{n-1}$, where $D_n < D_{n-1}$, the resultant image $I_{n-1} - I_n$ will isolate or emphasize those features lying at or about depth $D_{n-1}$.

Operations may also include image blending to highlight the differences and/or similarities between images.

Alternatively, processing may include performing feature detection on images captured with different polarization angles in order to detect feature(s) of interest, such as wrinkles or pigmented lesions. Once such features are detected in each of two or more images, a subtraction operation can then be performed to isolate or emphasize features lying at selected depths. Feature detection may include a variety of techniques, including performing a binary image segmentation procedure in which those image pixels representing detected features, such as wrinkles or pigmented lesions, are turned white, while the remaining pixels representing background tissue are turned black. Logical operations, such as AND or XOR operations, can then performed on these binary images to enhance features at different depths.

Figure 9:
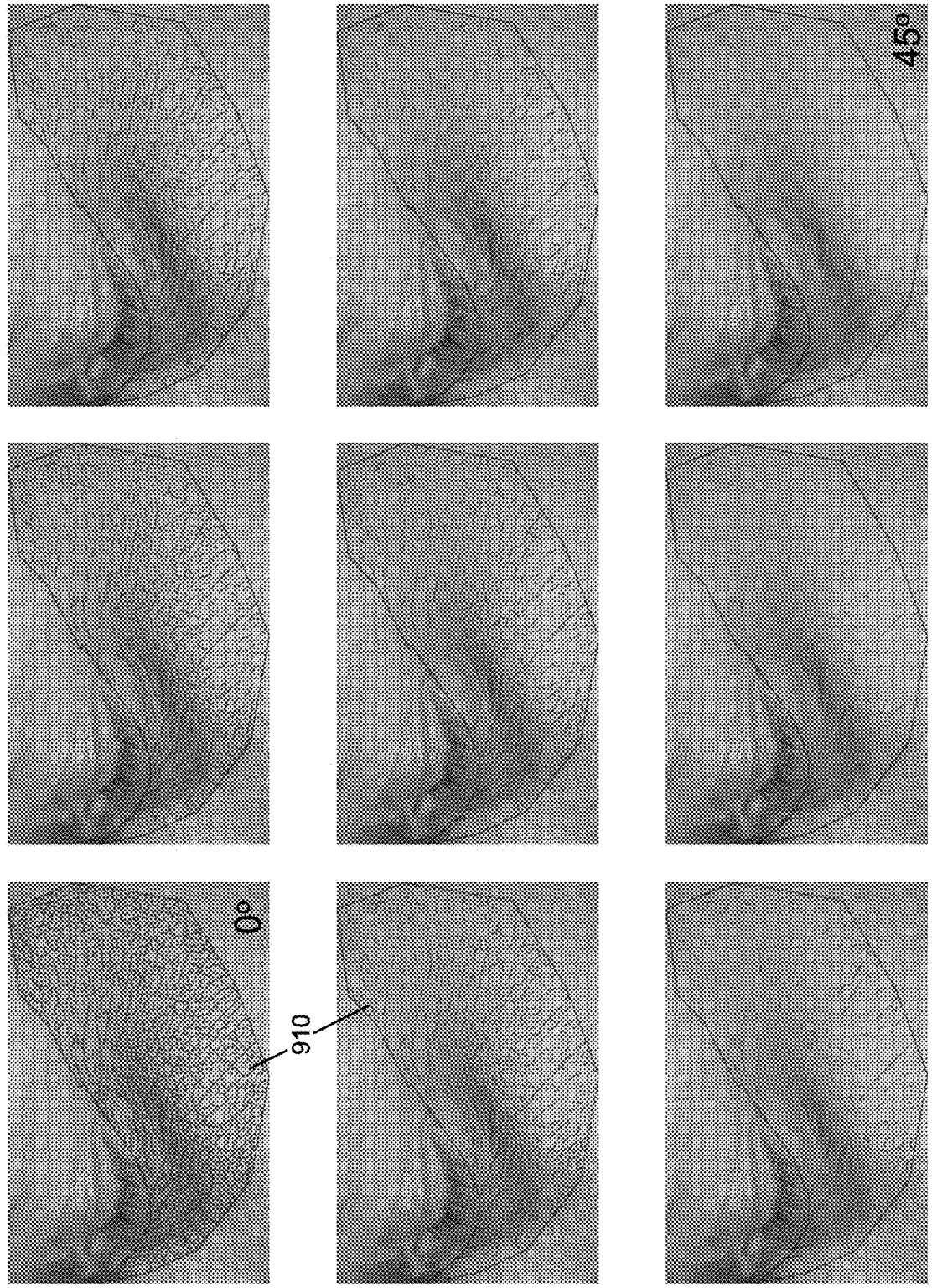
FIG. 9 shows an exemplary series of images generated in accordance with methods disclosed herein.

Further processing may include modifying one or more of the images to highlight features of interest. This may include generating indicia and overlaying them onto the image(s), among other possibilities. Exemplary such images are shown in FIG. 9, with illustrative indicia 910 thereon highlighting wrinkles within an area of interest. FIG. 9 shows a series of images captured at polarization angles from 0 degrees to 45 degrees, thereby better suited to imaging textural features, such as wrinkles, as opposed to subsurface features. As shown in this series of images, wrinkles, as expected, become less visible at the greater depths corresponding to the larger polarization angles.

Processing at 150 may also include the generation of 3D models using the captured images and corresponding depth information. From the depth information, a 3D reconstruction of the imaged skin area can be generated using the 2D images to show various skin layers and the skin feature distribution within these layers. Depth information can also be used to generate 3D image(s) of the skin surface topography showing valleys and ridges associated with wrinkles and pores, as well as 3D image(s) of deeper features, such as pigmented skin lesions or vascular structures. Preferably, user interactivity is provided allowing a user to manipulate or view 3D images from various angles and/or zoom levels. Preferably, the series of images as captured or as processed can be displayed such as in an animation or under user control, such as a slider or other suitable widget, to provide a moving presentation of information from different depths.

In addition or as an alternative to generating 2D or 3D images based on the captured images, processing 150 may include determining various measurements and/or metrics such as wrinkle scoring, pore size and count, skin texture/roughness, and pigmentation or vascular structure depth, among other possibilities. Both image and numerical information thus determined can be compared to information from images captured at a different time, such as to determine the efficacy of treatment, for example, with further metrics determined based on such differential analysis, among other possibilities.

It should be noted that some aspects of method 100 can be performed automatically, such as under program control, while others can be performed manually. For example, depending on the imaging apparatus used, several implementations of which are described below, the setting or changing of polarization angle at 110 and/or 140 can be done by user interaction with the apparatus, or can be done electronically or electromechanically under program control.

Further aspects of the present disclosure relate to devices that can provide imaging with variable polarization. In an exemplary embodiment, a dermatoscope device, such as described in U.S. Patent Application Publication No. 2014/0243685 A1 (incorporated herein by reference in its entirety), is modified in accordance with the principles of the present disclosure to provide variable polarization imaging.

Figure 3A:
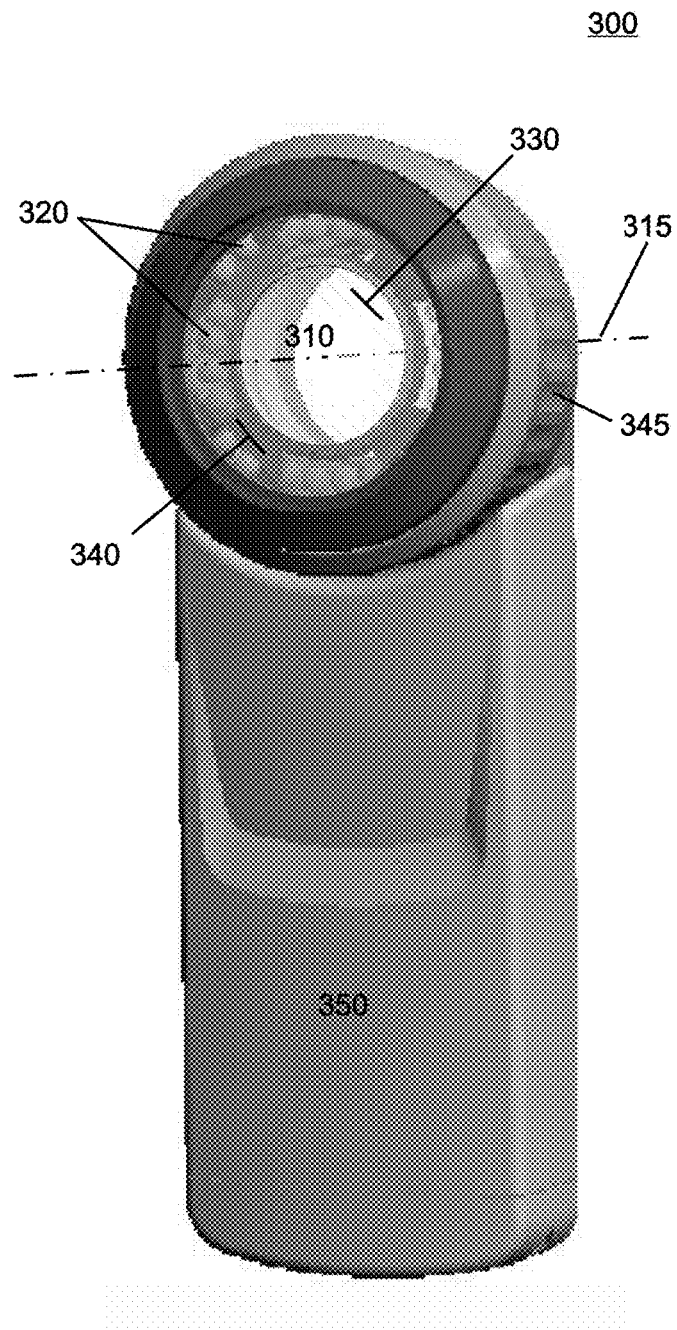
FIGS. 3A and 3B are front and back views, respectively, of an exemplary dermatoscope in accordance with the present disclosure.

More specifically, with reference to FIG. 3A, dermatoscope device 300 includes an optical opening 310 defining an optical path 315 through which skin may be viewed by a user or images thereof captured by a camera (not shown) attached to device 300. Optical opening 310 is surrounded by a plurality of light sources 320, which are selectively activatable by circuitry of the device 300, described further below.

A first polarizing filter 330 is arranged in line with optical path 315 for polarizing light passing through optical opening 310 of device 300. Additionally, a second polarizing filter 340 is arranged in line with light sources 320 for polarizing light emitted therefrom. In the exemplary device shown, polarizing filter 330 is generally circular in shape, corresponding to optical opening 310, and polarizing filter 340 is shaped as an annular ring, with an opening at least as large as optical opening 310 so as not to polarize light passing therethrough, while polarizing light emitted from light sources 320. Filters 330, 340 and optical opening 310 are generally coaxial.

In operation, light sources 320 are activated to emit light, which is polarized by polarizing filter 340, to illuminate the subject skin to be viewed with polarized light. Light reflected and/or emitted from the skin is viewed via path 315 through polarizing filter 330. This arrangement allows a user to view or an attached camera to capture skin features at depths corresponding to the polarization angle, the angle between the polarization orientations of detection polarizer 330 and source polarizer 340, as discussed above.

Light sources 320 may include, for example, light emitting diodes (LEDs) or the like, which emit white light or light of one or more colors. Polarizing filters 330, 340 may also have wavelength-selective properties or non-polarizing, wavelength-selective filters can be included in line with one or both polarizing filters 330, 340.

Figure 3B:
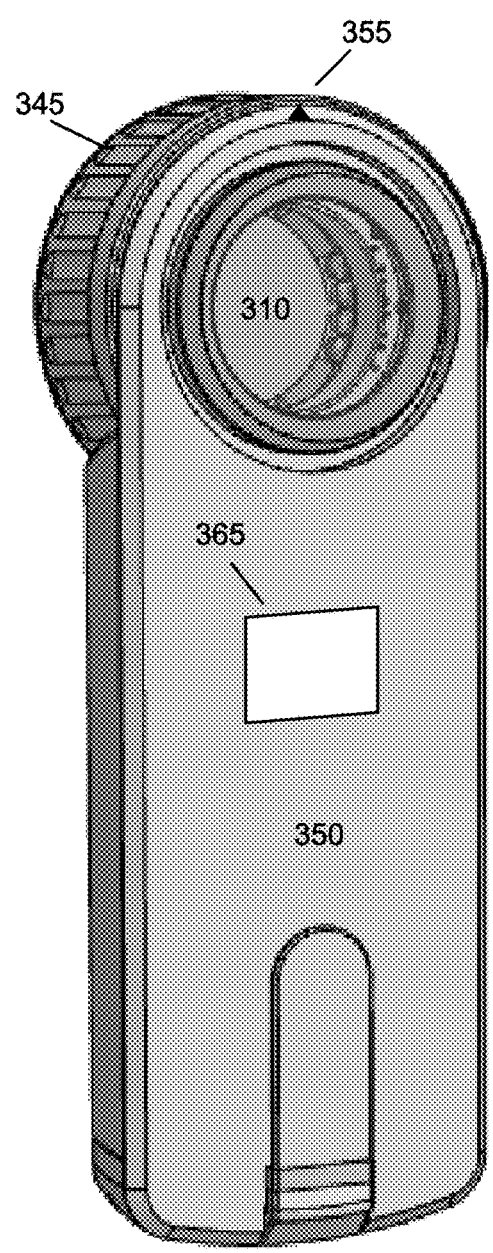
Figure 4A:
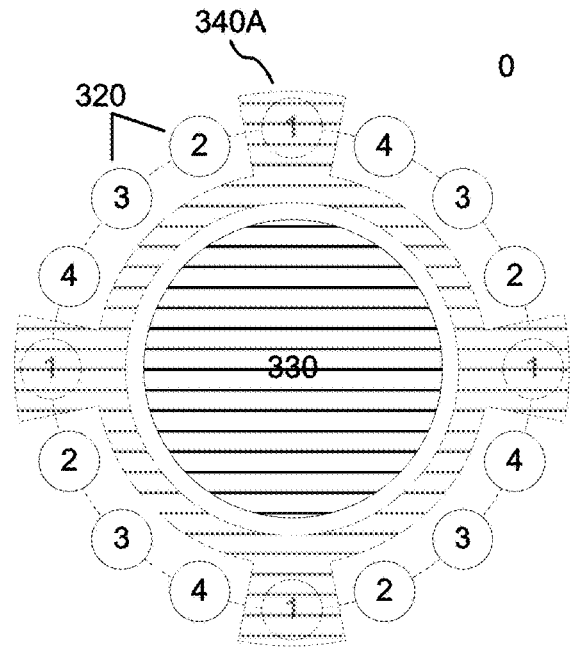
FIGS. 4A through 4D are schematic representations of polarizers and light sources arranged in an exemplary device in accordance with the present disclosure.
Figure 4B:
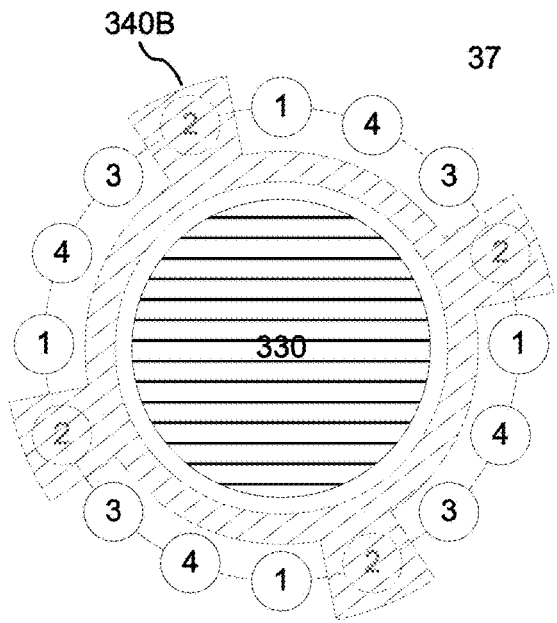
Figure 4C:
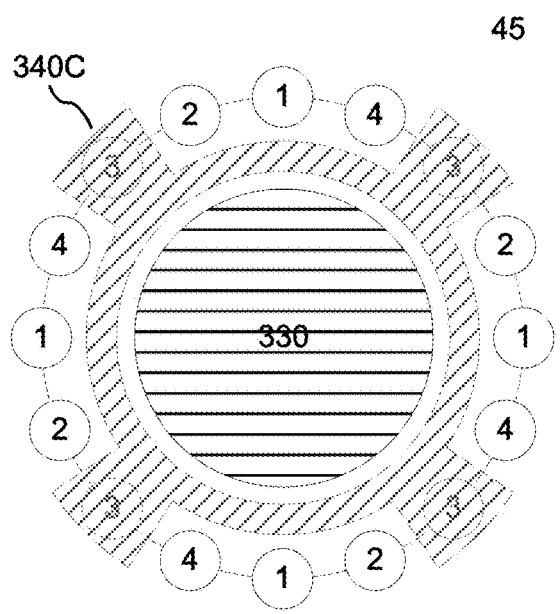
Figure 4D:
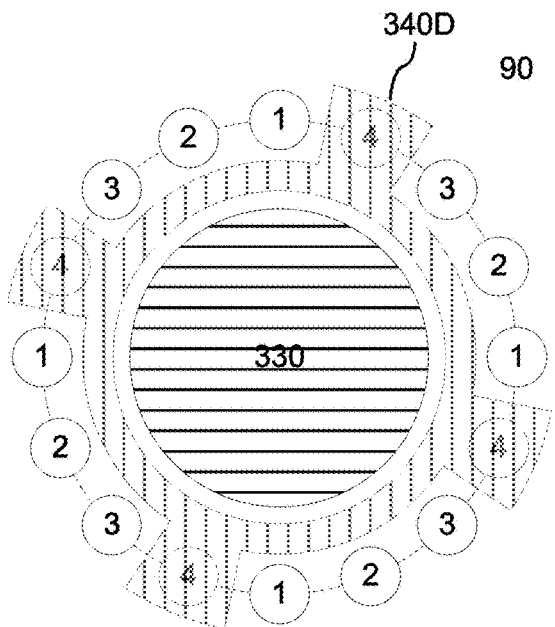

In exemplary implementations, either or both polarizing filters 330, 340 are rotatable about their centers so as to allow the polarization angle to be varied. For instance, detection polarizing filter 330 can be stationary, whereas source polarizing filter 340 can be rotated, such as by rotating a bezel 345 coupled thereto. Preferably, some indication of the selected polarization angle is provided, such as, for example, by providing markings on bezel 345 and a pointer 355 on a stationary part such as housing 350 relative to which the bezel 345 is rotatable. As shown in FIG. 3B, such markings and pointer are preferably provided on the back of device 300 so that a user can readily see them while the device is placed against an area of skin to be imaged.

The position of bezel 345 and thus the polarization angle, can also be determined by an electronic sensor or detector, such as an optical encoder or the like, and the polarization angle indicated on a display 365, preferably on the back of device 300, among other possibilities. Display 365 may also be used to display other information, such as an estimated depth corresponding to the selected polarization angle, device status, or other information. In addition, device 300 can be provided with a wired or wireless data communications interface via which polarization angle and/or other information can be provided to an image capture device or system, which can associate that information with captured images, such as by tagging or labeling the images with the information, or saving the information as image metadata, among other possibilities.

The movement of bezel 345 may also have preselected indents for desired or commonly used polarization angles, such as 0, 37, 45 and 90, among others.

Additionally or alternatively, instead of being rotated by user rotation of a bezel 345, polarizer 330 and/or polarizer 340 can be rotated using an electromechanical arrangement controlled by circuitry of device 300. The latter has the advantage of allowing for programmed control of the image capturing procedure. In illustrative operation of such implementations for example, a series of images with different polarization angles can be captured in rapid succession, with minimal or no movement of the subject area between images.

A further exemplary implementation of dermatoscope device 300, one that can provide variable polarization imaging with stationary polarizers, will now be described with reference to FIGS. 4A-4D. As schematically depicted therein, 16 light sources 320 are arranged about the device's optical opening 310, in which detection polarizer 330 is fixedly arranged. The 16 light sources are arranged in four groups 1-4 of four light sources each. As shown in the exemplary implementation of FIGS. 4A-4D, the light sources of each of the four groups are preferably distributed generally uniformly about the viewing opening; i.e., generally with an angular displacement of 360*G/N degrees, where N is the number of light sources and G is the number of groups, relative to the adjacent light sources of the same group. For the case of four groups of 16 light sources, the light sources assigned to the same group are thus 90 degrees apart, as shown. The individual light sources 320 are also shown in FIGS. 4A-4D as being evenly distributed, with an angular displacement therebetween of 360/N degrees, or 22.5 degrees in the case of 16 light sources.

The light emitted from each group of light sources is polarized by a respective polarizing filter 340A-340D with a respective polarization orientation of 0, 37, 45 or 90 degrees relative to the orientation of polarizer 330 arranged in the viewing opening. Polarizing filters 340A-340D replace filter 340 shown in FIG. 3A.

When on, the light sources 320 in each group are activated together, with one group of light sources being on and the other groups of light sources being off at any given time. As such, by selectively activating one of the four groups of light sources 320, the device 300 will emit polarized light with a corresponding polarization angle (i.e., the angle between the polarization orientation of the corresponding source polarizer 340A-340D and the polarization orientation of the detection polarizer 330) of 0, 37, 45, or 90 degrees.

More specifically, dermatoscope device 300 can be used for parallel-polarized imaging, in which the polarization angle is 0, by activating the light sources of group 1, whose emitted light is polarized by polarizer 340A. Device 300 can also be used for cross-polarized imaging, in which the polarization angle is 90, by activating the light sources of group 4, whose emitted light is polarized by polarizer 340D.

Additionally, dermatoscope device 300 can be used for imaging with intermediate polarization angles, such as 37 degrees, by activating the sources of group 2, whose light is polarized by polarizer 340B, or with a polarization angle of 45 degrees, by activating the sources of group 3, whose light is polarized by polarizer 340C. Imaging with a polarization angle of 37 degrees provides an image similar to a standard photograph, i.e., an image captured without any polarizer. Imaging with a 45-degree polarization angle captures images at depths shallower than the cross-polarized image, in which the polarization angle is 90 degrees.

Figure 5:
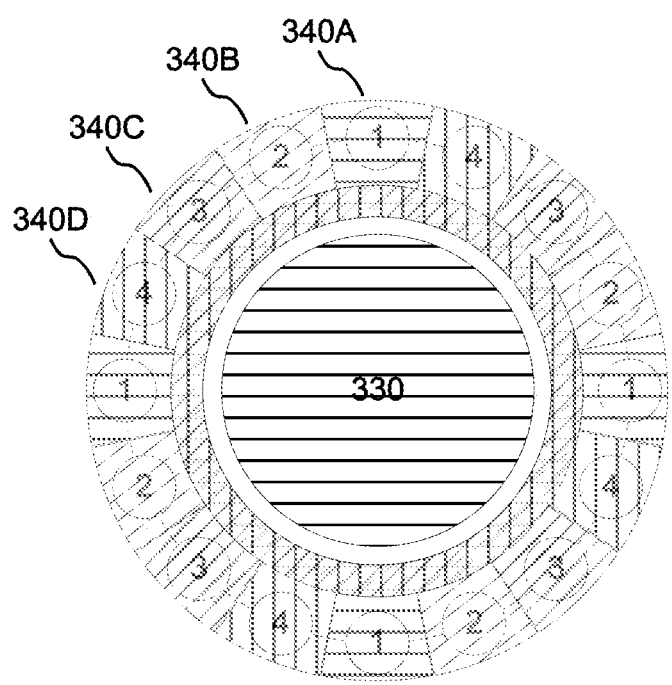
FIG. 5 is a combined schematic representation of the polarizers of FIGS. 4A-4D.

It should be noted that for purposes of clarity, the polarizers 340A-340D are shown in isolation in FIGS. 4A-4D, respectively. FIG. 5 shows a stacked arrangement of the polarizers, in accordance with an exemplary implementation of dermatoscope device 300.

Figure 6:
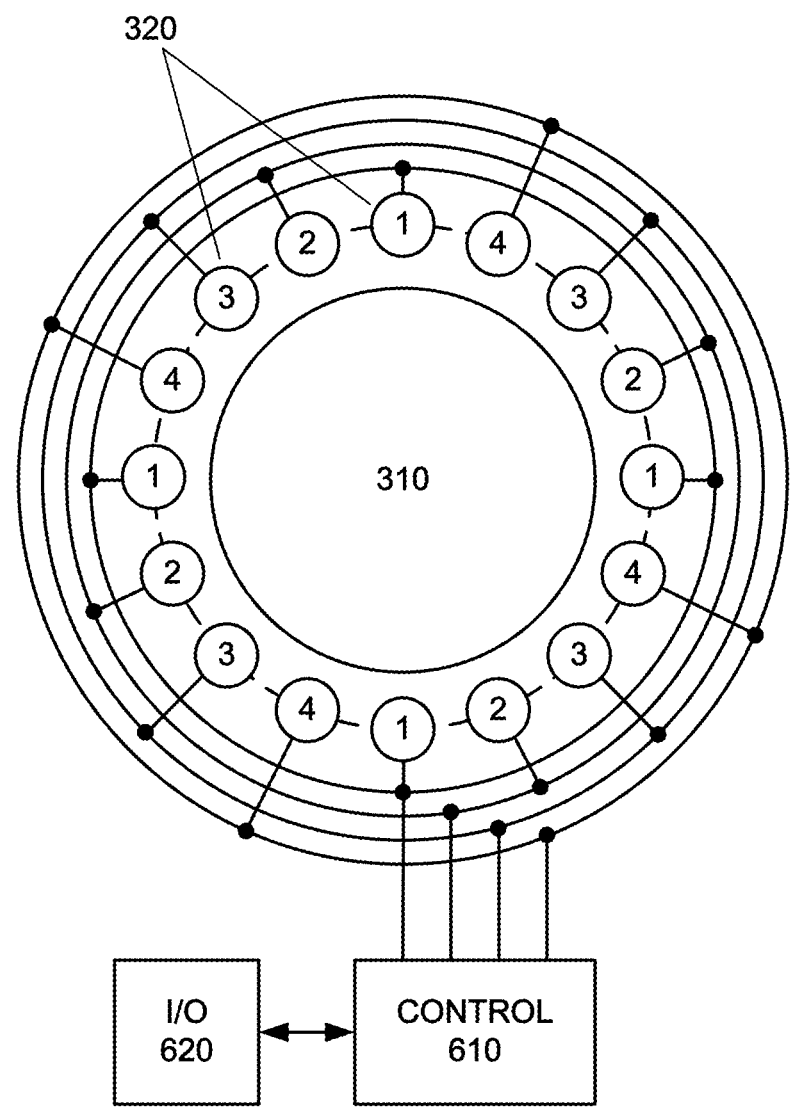
FIG. 6 is a schematic representation of circuitry for an exemplary device in accordance with the present disclosure.

FIG. 6 schematically shows a circuit for controlling the light sources 320 of device 300. As discussed, light sources 320 are arranged in four groups 1-4, and as shown in FIG. 6 are wired accordingly so that each group 1-4 is controlled independently of the other groups by control circuitry 610. Input/output (I/O) circuitry 620, coupled to control circuitry 610, may include buttons, switches, a touchscreen, or the like that a user can actuate to indicate a desired operating mode such as which polarization angle to implement. Based on signal(s) from I/O 620, control circuitry 610 enables the group 1-4 of light sources 320 corresponding to the desired polarization angle. I/O 620 may also include an indicator or display to indicate the selected polarization angle. Control circuitry 610 may include a microcontroller, one or more integrated circuits and/or discrete circuitry. In addition or as an alternative to the above-mention user I/O elements, I/O circuitry 620 may include a data communications interface, such as a wired or wireless serial or parallel interface, or the like. Such an interface can be used to control device 300, including selecting a polarization angle, and/or to provide information such as polarization angle and/or other information from device 300 to an image capture device or system, which can associate that information with captured images, such as by tagging or labeling the images with the information, or saving the information as image metadata, among other possibilities.

Multiple variations are contemplated for different implementations in accordance with the present disclosure. For example, the number, arrangement and/or grouping of light sources can vary from those of exemplary device 300 shown and described above. For instance, the light sources 320 can be arranged about the optical opening 310 at different radial distances, with two or more adjacent light sources in the same group (e.g., each light source 320 comprises two or more light sources), and/or in more or fewer than four groups. As can be appreciated, a larger number of groups of light sources allows for more polarization angles and thus greater depth resolution. Additionally, light sources of the same group may also be displaced from each other at more or less than 90 degrees. Also, while individual light sources 320 are shown in FIGS. 4A-4D as being evenly distributed, it is possible, for example, for multiple light sources of the same group to be more closely spaced together relative to adjacent light sources of a different group; e.g., each light source 320 can be implemented as a cluster of multiple light sources. Moreover, different groups of light sources can be arranged at different radial distances from the optical opening 310. Furthermore, different groups of light sources may have different numbers of light sources.

Similarly, different polarization angles, or no polarization, can be implemented than those implemented in device 300 described above. For example, one group of light sources can have no corresponding polarizer, thereby providing illumination with no polarization. Additionally, instead of implementing a polarization angle of 37 degrees as described, a polarization angle between 45 and 90 degrees can be implemented to provide additional depth resolution. Alternatively, since imaging with a polarization angle of 37 degrees provides an image very similar to a standard photograph, the corresponding source polarizer (340B) may be eliminated. It should be noted, however, that each polarizer will block light that does not have the same polarization as the polarizer. As such, unpolarized light having passed through a polarizer will have a lower intensity than it would if it had not. Therefore, for applications in which it is desirable to maintain similar illumination intensity for all images viewed or captured with device 300, it may be necessary or preferable to keep the 37 degree source polarizer 340B. Alternatively, to compensate for this difference in intensity, those light sources 320 emitting light that is not polarized can be set or controlled (such as by control circuit 610) to emit light with lower intensity than light sources whose light is polarized.

Additionally, while source polarizers 340A-340D have been shown as single polarizing elements covering a respective group of light sources 320, other implementations of source polarizers consistent with the present disclosure are possible. For example, individual polarizer elements can be implemented for each light source 320, with measures taken to ensure that the orientations of the polarizer elements for light sources in the same group are in alignment with each other. Similarly, light sources 320 can be implemented using polarized light sources, such as polarized LEDs, with their polarization orientations relative to that of polarizer 330 determined by their placement on a circuit board, housing, or other structure to which they are mounted, among other possibilities.

In other implementations, polarizers 340A-340D can be implemented in which the portions thereof covering the light sources 320 are connected by an outer as opposed to an inner ring of material, or as annular rings with openings for those light sources whose light they are not to polarize.

It should also be noted that the above described implementations of variable polarization can be adapted to a variety of dermatoscopic devices having illumination, such as for example, the VISIOMED D200EVO and VEOS HD2 and DS3 devices from Canfield Scientific Inc., as well as other devices.

In further exemplary implementations, a VISIA imaging system from Canfield Scientific, Inc., or the like, is modified to incorporate variable polarization illumination and/or detection polarization to provide various polarization angles between illumination and detection, as described above. Such variable polarization can be implemented, for example, with a filter wheel or the like, allowing polarizers of different polarization orientations to be placed selectively in front of the illumination source(s) and/or image capture device (camera) of the VISIA system. Alternatively, a polarizer in front of the illumination source and/or capture device can be rotated to change its polarization orientation relative to the imaged area. In an exemplary method, such as method 100 described above with reference to FIG. 1, a series of images can be captured with different polarization angles by changing or rotating one or both of the source or detection polarizers. The changing of polarization angle can be done manually, or using an electromechanical arrangement, under user or program control.

As can be appreciated, implementations of the methods and apparatuses of the present disclosure can be used for a variety of applications, including, for example, skin topography analysis, such as for assessing skin quality, including for example, evaluating wrinkles, pores, skin texture, and raised lesions such as acne. In such applications, in which the focus is on superficial features, multiple images are captured with various polarization angles from 0 to 45 degrees (and more specifically 0 to 37 or 37.5 degrees) to examine skin surface texture.

Implementations of the methods and apparatuses of the present disclosure can be used for subsurface skin examination. With polarization angles between 90 and 37.5 degrees, subsurface information may be obtained. Better depth resolution can be obtained particularly with polarization angles in the range of 70 to 90 degrees. Imaging with such polarization angles can be used, for example, to evaluate how deep the pigment of a lesion is or how deeply a vascular structure sits. This is useful in determining the depth of potentially cancerous lesions, among other applications. In dermoscopic evaluation of skin lesions, such as melanoma, knowing the lesion depth and the structure/density of pigmentation at different depths will help provide a more accurate diagnosis.

It is contemplated that imaging devices can be implemented with various ranges and/or sets of polarization angles, such as, for example, a general purpose device with a wide range of polarization angles, or more specialized devices, such as one or more devices for superficial skin analysis with polarization angles between 0 and 45, and one or more devices for deeper skin analysis with polarization angles between 45 and 90, among other possibilities.

Figure 7:
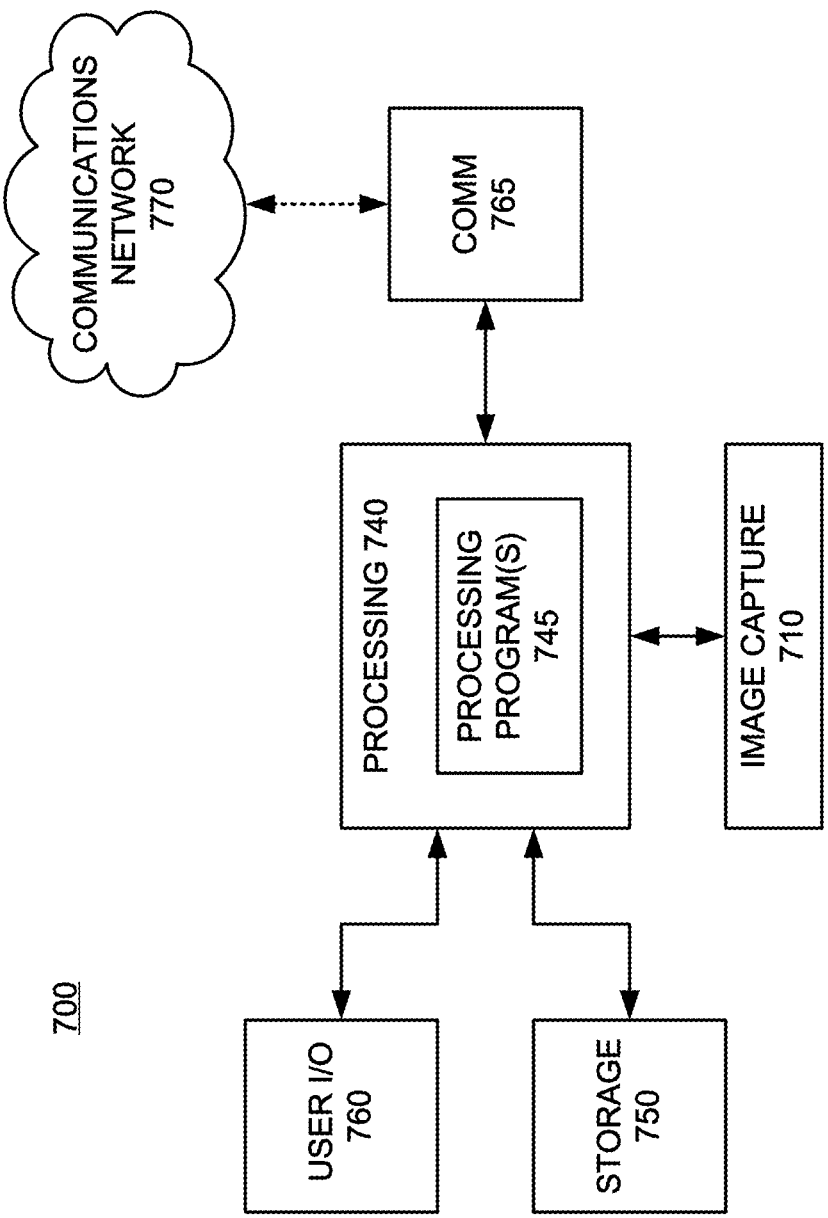
FIG. 7 is a schematic representation of an exemplary system in accordance with the present disclosure.

Turning now to FIG. 7, there is shown in schematic form an exemplary imaging system 700 in accordance with the present disclosure. As shown in FIG. 7, components of system 700 include an image capture apparatus 710 coupled to processing circuitry 740. Image capture apparatus 710 may include, for example: a variable polarization dermatoscope, such as described above, attached to a camera; a dermatoscope with image capturing capabilities, such as Canfield Scientific Inc.'s VISIOMED D200EVO and VEOS DS3 devices modified to provide variable polarization imaging as described herein; a mobile device with image capturing capabilities, such as a smartphone or tablet computer, with attachment(s) for providing variable polarization imaging as described herein; or a skin imaging system, such as a Canfield Scientific Inc. VISIA system, among other possibilities.

Advantageously, the captured images can be single mode or multimodal—including, for example, those from standard white light, polarized light, and/or fluorescent light—captured at selected wavelengths and/or illuminated with selected wavelengths of light.

Images captured by image capture apparatus 710 are provided to processing circuitry 740 for processing as described above. Of further advantage, processing circuitry 740 may also control image capture apparatus 710, for example, by controlling one or more aspects of the image capture and/or illumination of the subject, such as exposure, modality, including whether or not to use polarization and with which polarization angle, or other filtering, among others.

Images may also be provided to processing circuitry 740 from other sources and by other means. For example, images may be provided via communications network 770, or in a non-transitory storage medium, such as storage 750.

Processing circuitry 740 may be coupled to storage 750, for storing and retrieving images, among other data, and/or programs, software, and firmware, among other forms of processing instructions; and to input/output devices 760, such as a display device and/or user input devices, such as a keyboard, mouse, touchscreen, or the like. Processing circuitry 740 may also be coupled to a communications module 765 for interconnection with a communications network 770, such as a local network and/or the Internet, for transmitting and receiving images and/or data, and/or receiving commands, software updates or the like. Processing circuitry 740, storage 750, I/O 760, and/or communications module 765 may be implemented, for example, with one or more computers, workstations, processors, or the like, operating in accordance with one or more programs 745 embodied in a compatible, non-transitory, machine-readable storage medium. Program(s) 745 may be stored in storage 750 and/or other memory devices (not shown), and provided therefrom and/or from communications network 770, via communications module 765, to processing circuitry 740 for execution. Methods in accordance with the present disclosure, such as method 100 described above with reference to FIG. 1, can be implemented by execution of one or more programs 745.

The various components of system 700 may be connected via any suitable wired or wireless connections.

It should be noted that the exemplary system 700 illustrates just one of a variety of possible arrangements contemplated by the present disclosure. For example, the various components of system 700 need not be co-located. For instance, image capture apparatus 710 and I/O devices 760 can be located in a practitioner's office and processing circuitry 740 and storage module 750 can be remotely located, functioning within a telehealth framework, or can be "cloud-based," interacting with image capture apparatus 710 and I/O devices 760 over communications network 770. In other exemplary arrangements, I/O devices 760 can be remotely located from image capture apparatus 710, thereby allowing a user to remotely examine subjects' images, such as in a telehealth arrangement.

In other implementations, system 700 can be implemented with a portable or mobile computing device having image capture apparatus 710 integrated therein, such as a tablet computer, smartphone, a Canfield VEOS DS3 device, or the like, modified or provided with attachment(s) to provide variable polarization imaging as described herein.

The foregoing merely illustrates principles of the present disclosure and it will thus be appreciated that those skilled in the art will be able to devise numerous alternative arrangements which, although not explicitly described herein, embody the principles of the disclosure and are within its spirit and scope. In addition, as can be appreciated, while specific implementations have been described above with respect to the analysis of skin, there are multiple applications entailing the capture and/or analysis of images that could benefit from the techniques disclosed herein, including applications involving tissue in other parts of human and/or animal bodies, in vivo or in vitro, among other possibilities.

Additionally, although illustrated as single elements, each block, step, or element shown may be implemented with multiple blocks, steps, or elements, or various combinations thereof. Also terms such as "software," "application," "program," "firmware," or the like, are intended to refer, without limitation, to any instruction or set of instructions, structure, or logic embodied in any suitable machine-readable medium. It is to be understood that numerous modifications may be made to the illustrative embodiments and that other arrangements may be devised without departing from the spirit and scope of the present disclosure.

At this point, while this disclosure has been presented using some specific examples, those skilled in the art will recognize that the teachings of this disclosure are not thus limited. The foregoing merely illustrates principles of one or more inventions and it will thus be appreciated that those skilled in the art will be able to devise numerous alternative arrangements which, although not explicitly described herein, embody the principles of the one or more inventions and are within the spirit and scope thereof. It is to be understood that numerous modifications may be made to the illustrative embodiments and that other arrangements may be devised without departing from the spirit and scope of the one or more inventions as defined by the appended claims.

What is claimed:

1. A skin analysis method comprising:
   obtaining at least three images from at least three respective depths of an area of skin, at least two of the depths being below a surface of the area of skin, each image having been captured through a detection polarization and with illumination of a source polarization, the detection and source polarizations having respective orientations defining a polarization angle therebetween, the polarization angle being different for each of the at least three images; and
   processing the at least three images to generate at least one further image or further information derived from the at least three images, including:
      determining a relative depth of at least two of the images based on the polarization angles with which the images were captured and on skin type.

2. The method of claim 1, wherein obtaining the at least three images includes:
   illuminating the skin with the illumination having the source polarization,
   capturing each of the images through the detection polarization, and
   changing at least one of the source polarization orientation or the detection polarization orientation between capturing each image.

3. The method of claim 1, wherein processing the at least three images includes generating an image indicating one or more features in at least one of the images.

4. The method of claim 1, wherein processing the at least three images includes generating a three-dimensional image.

5. A non-transitory computer-readable storage medium having stored thereon a computer program comprising instructions for causing a skin analysis apparatus to perform the method of claim 1.

6. A skin analysis apparatus comprising:
   circuitry configured to:
      obtain at least three images from at least three respective depths of an area of skin, at least two of the depths being below a surface of the area of skin, each image having been captured through a detection polarization and with illumination of a source polarization, the detection and source polarizations having respective orientations defining a polarization angle therebetween, the polarization angle being different for each of the at least three images; and
      process the at least three images to generate at least one further image or further information derived from the at least three images, including:
         determining a relative depth of at least two of the images based on the polarization angles with which the images were captured and on skin type.

7. The apparatus of claim 6, wherein obtaining the at least three images includes:
   illuminating the skin with the illumination having the source polarization,
   capturing each of the images through the detection polarization, and
   changing at least one of the source polarization orientation or the detection polarization orientation between capturing each image.

8. The apparatus of claim 6, wherein processing the at least three images includes generating an image indicating one or more features in at least one of the images.

9. The apparatus of claim 6, wherein processing the at least three images includes generating a three-dimensional image.

* * * * *